United States Patent [19]

Macrae et al.

[11] Patent Number: 4,861,716
[45] Date of Patent: Aug. 29, 1989

[54] REARRANGEMENT PROCESS

[75] Inventors: Alasdair R. Macrae, Bromham; Peter How, Yelden, both of England

[73] Assignee: Lever Brothers Company, New York, N.Y.

[21] Appl. No.: 111,239

[22] Filed: Jul. 21, 1987

Related U.S. Application Data

[60] Division of Ser. No. 817,751, Jan. 2, 1986, Pat. No. 4,719,178, which is a continuation of Ser. No. 490,461, May 2, 1983, abandoned.

[30] Foreign Application Priority Data

Apr. 30, 1982 [GB] United Kingdom ............... 8212688

[51] Int. Cl.$^4$ ..................... C12P 7/62; C12P 7/64; C12N 11/14; C12N 1/20
[52] U.S. Cl. ..................... 435/134; 426/33; 435/135; 435/176; 435/198
[58] Field of Search ............... 435/134, 135, 176, 198; 426/33

[56] References Cited

U.S. PATENT DOCUMENTS

| | | | |
|---|---|---|---|
| 4,062,882 | 12/1977 | Sen Gupta | 260/428.5 |
| 4,275,081 | 6/1981 | Coleman et al. | 435/134 |
| 4,364,868 | 12/1982 | Hargreaves | 435/134 |
| 4,416,991 | 11/1983 | Matsuo et al. | 435/134 |
| 4,719,178 | 1/1988 | Macrae et al. | 435/135 |

FOREIGN PATENT DOCUMENTS

| | | | |
|---|---|---|---|
| 0064855 | 11/1982 | European Pat. Off. | 435/134 |
| 0069599 | 1/1983 | European Pat. Off. | 435/134 |

Primary Examiner—Robert A. Wax
Attorney, Agent, or Firm—Milton L. Honig

[57] ABSTRACT

In a continuous interesterification process a fatty acid ester reactant, preferably a glyceride and optionally including free fatty acid, is contacted with an enzyme as interesterification catalyst which is preferably 1,3-selective and precipitated on an inert particulate support. The catalyst is packed in a fixed bed with contact times less than 2 hours which are sufficient to effect interesterification. The process is useful for producing POSt- and StOSt-rich fats suitable for use as cocoa butter substitute fats.

5 Claims, No Drawings

REARRANGEMENT PROCESS

This is a divisional application of Ser. No. 817,751 filed Jan. 2, 1986, now U.S. Pat. No. 4,719,178 which is a continuation application of Ser. No. 490,461, filed May 2, 1983, now abandoned.

This invention relates to interesterification particularly using microbial lipases as catalysts.

Interesterification is a process which is used in the oils and fats industry to modify the properties of triglyceride mixtures, in particular their consistency. In this process a catalyst such as sodium metal or sodium methoxide is used to promote acyl migration between glyceride molecules so that the products consist of glyceride mixtures in which the fatty acyl residues are randomly distributed amongst the glyceride molecules.

Extracellular microbial lipases (glycerol ester hydrolases) are enzymes which in nature catalyse the hydrolysis of fats to give free fatty acid, partial glycerides and glycerol. The reaction is reversible and the enzymes can be shown to catalyse the formation of glycerides from glycerol and free fatty acid under certain conditions. The synthetic reaction is of no significance in the biosynthesis of oils and fats.

The naturally-occurring triglycerides of long chain fatty acids are water-insoluble, and lipases are characterised by the ability rapidly to catalyse the hydrolysis of ester bonds at the interface between the insoluble substrate phase and the aqueous phase in which the enzyme is soluble. Thus the enzymes catalyse the hydrolysis of a wide range of insoluble fatty acid esters, although glycerides are normally the preferred substrates, while hydrolysis of water-soluble carboxylic acid esters by true lipases is very slow. The lipase reactions are reversible, and because of this reversibility hydrolysis and resynthesis of glycerides occurs when lipases are incubated with oils and fats. This hydrolysis and resynthesis causes acyl migration between glyceride molecules and gives interesterified products. Under conditions in which the amount of water in the reaction system is restricted, hydrolysis of the fat can be minimised so that lipase catalysed interesterification becomes the dominant reaction.

Mixtures of triglycerides and free fatty acid can also be used as reactants for lipase-catalysed interesterification reactions. In these cases free fatty acid exchanges with the acyl groups of the triglycerides to produce new triglycerides enriched in the added fatty acid. With non-specific lipases enrichment of all three glyceride positions occurs, but with 1,3-specific lipases the reaction is confined to the 1- and 3-positions of the glycerides. If a fatty acid-specific lipase is used a particular fatty acid from a mixture of fatty acids can be selectively introduced.

The microbial lipases can be placed in three groups according to their specificity of reactivity. The first group shows no marked specificity both as regards the position on the glycerol molecule which is attacked and the nature of the fatty acid released. These lipases can catalyse the complete breakdown of triglycerides by hydrolysis to free fatty acid and glycerol, but diglycerides and monoglycerides appears as intermediates in the reaction. Examples of enzymes of this types are the lipases from *Candida cylindracae, Corynebacterium acnes* and *Staphylococcus aureus*.

The second group of lipases catalyses the specific release of a particular type of fatty acid from glyceride molecules. Most extracellular microbial lipases show little fatty acid specificity when incubated with natural oils and fats. However the lipase produced by *Geotrichum candidum* has been shown to possess a very marked specificity for the hydrolysis of esters of a particular type of long chain fatty acid. The substrate specificity of this enzyme has been studied by the groups of Alford, Jensen and Franzke, who showed that the lipase preferentially releases from triglycerides long chain fatty acids containing a cis double bond in the 9-position. Saturated fatty acids and unsaturated fatty acids without a double bond in the 9-position were only slowly released.

The third group of lipases catalyse the release of fatty acid only from specific positions of glycerides. From lipases reactive in the 1- and 3-positions only, triglycerides are hydrolysed to give free fatty acids, 1,2(2,3)-diglycerides and 2-monoglycerides as reaction products. Because 1,2(2,3)-diglycerides, and especially 2-monoglycerides are chemically unstable and undergo acyl migration to give 1,3-diglycerides and 1(3)-monoglycerides respectively, prolonged incubation of a fat with a 1,3-specific lipase will give complete breakdown of some of the triglycerides with the formation of glycerol. 1,3-specificity is common amongst microbial lipases, and examples of enzymes from this group are the lipases from *Aspergillus niger, Mucor javonicus* and various Rhizopus species. No example of enzyme with 2-specificity has as yet been detected.

The stereospecificity (i.e. relative catalytic activity of the $sn$-1 and $sn$-3 positions of the glycerol moiety) of *Rh. arrhizus* lipase has been investigated. It was shown that fatty acid is released at a similar rate from the sn-1 and sn-3 positions of enantiomeric forms of phosphatidylcholine, therefore *Rh. arrhizus* lipase and in all probability other microbial lipases show no stereospecificity. The positional specificity of the 1,3-specific lipases probably results from an inability of the sterically-hindered esters of secondary alcohols, e.g. those of the 2-position of glycerol, to enter the active site of the enzyme.

If a non-specific lipase is used to catalyse the interesterification of a triglyceride mixture, the triglycerides produced are similar to those obtained by chemical interesterification. However, with a 1,3-specific lipase as catalyst, acyl migration is confined to the 1- and 3-positions and a mixture of triglycerides which is unobtainable by chemical interesterification is produced.

The interesterification reaction is accompanied by the formation as by-products of diglyceride and additional free fatty acid. Examination of the products formed during a stirred tank interesterification reaction using a 1,3-specific enzyme as catalyst shows that most of the diglyceride and additional free fatty acid is formed in the first hour of the reaction. During this period an equilibrium between triglycerides, water, 1,2-diglyceride and free fatty acid is established. The subsequent slow generation of more diglyceride can be attributed to the formation of 1,3-diglyceride by a slow isomerisation reaction. This isomerisation reaction leads to a loss of total triglyceride, and in some cases to a lowering of the proportion of valuable triglycerides in the total triglyceride fraction as a result of an interesterification of 1,3-diglyceride with triglyceride. Because the generation of some of the by-products is dependent on the slow isomerisation reaction an advantage can be gained by use of reaction conditions in which the contact time between the reactants and the catalyst is short. These conditions are readily achieved in a continuously operated packed bed reactor.

The present invention therefore provides a continuous interesterification process in which a water-insoluble organic liquid comprising fatty reactants including a fatty acid ester is contacted with a lipase enzyme as interesterification catalyst and a small amount of water to activate the catalyst, wherein the catalyst is packed in a fixed bed in which a mean residence time of the reactant is less than 2 hours which is sufficient to effect interesterification. The process is particularly suitable for the rearrangement of fats or glyceride oils in which a catalyst comprising a positionally specific microbial lipase is used with a small amount of water to activate the catalyst, and in which the mean residence time with the catalyst is less than 2 hours. Because of the short residence time, very little isomerisation of 1,2-diglyceride to 1,3-diglyceride occurs and consequently the yield of triglyceride obtained from a packed bed reactor in accordance with the invention is higher than that obtained from batch processes in stirred tanks. Preferably the mean residence time is from 1 minute to 30 minutes, preferably 10 to 30 minutes, particularly about 20 minutes and preferably at 10° to 60° C., preferably 20° to 50° C. Mean residence time is defined by Levenspiel in Chemical Reaction Engineering, 2nd Ed., (1972), Wiley, at page 528, and measures the time occupied by the reaction liquid in the voids of the bed. It therefore measures the contact time of the liquid with the catalyst.

The ability to produce novel triglyceride mixtures using positionally specific lipases is of interest to the oils and fats industry because some of these mixtures have properties which make them valuable. This is illustrated by the following.

1,3-specific lipase-catalysed interesterification of 1,3-dipalmitoly-2-monoleine (POP), which is the major triglyceride of the mid-fraction of palm oil, with either stearic acid or tristearin gives products enriched in the valuable 1-palmitoyl-3-stearoyl-2-monoleine (POSt) and 1,3-distearoyl-2-monoleine (StOSt). POSt and StOSt are the important components of cocoabutter, and therefore it is possible by the interesterification reaction to produce a valuable cocoabutter equivalent from cheap starting materials.

The catalysts used for enzymatic interesterification are suitably prepared by addition of solvent such as acetone, ethanol or methanol to a slurry of an inorganic particulate material such as kieselguhr, hydroxylapatite or alumina in buffered lipase solution. The precipitated enzyme coats the inorganic particles, and the lipase-coated particles are collected by filtration, dried and stored in a dried form. In the dried form the particles are inactive as interesterification catalysts, and to obtain catalytic activity it is necessary to activate the catalyst. Such processes are described in British patent specification no. 1,577,933, European patent specification no. 0 034 065, European patent specification no. 0 069 599 and European patent specification no. 0 064 855, in which the particles are activated by addition of about 10% water prior to their use in the interesterification reaction systems. Preferably also the reaction is conducted in the presence of a small amount of water dissolved in the organic phase. For this purpose at least part of the liquid may be pre-saturated, for example by contact with a packed bed of an inert particulate material, e.g. Celite, preferably to an amount from 40 to 70% of the saturation amount, which is preferably less than 1%. In any event the solubility of water in the reaction medium should be limited to retain the activity of the catalyst.

As in the method described therein, preferably the interesterification process of the present invention is carried out at 0°–60° C. in solution in an inert organic solvent, particularly a hydrocarbon or mixture thereof, in a concentration of reactants from 5–50% by weight. Any free fatty acid in the reactant solution is preferably present in an amounts of 10%–50% by weight of the triglyceride present. The reaction is applicable to a wide range of triglyceride oils and fats of animal, vegetable or marine origin and may be applied also to their fractionated and hydrogenated derivatives and to synthetic glycerides. Examples of oils include palm and shea. Fatty acids used preferably are saturated and contain 3 to 20 carbon atoms, particularly myristic, palmitic and stearic acids.

EXAMPLE 1

100 parts by weight of a mid-fraction of palm oil and 40 gms myristic acid, dissolved in 220 parts by weight of petroleum ether, BP 100°–120° C., were interesterified at 40° C. using an *Aspergillus niger* lipase catalyst in a continuous operation in accordance with the invention and by way of comparison, batchwise in a control experiment. The catalyst was prepared in accordance with the method described in Example 2 of British patent specification 1,577.933, from lipase AP6 supplied by Amano Pharmaceutical with an activity of 940 U/gm. The catalyst on Celite was wetted with 8% its weight of distilled water 24 hours before use.

In the batch experiment 10 parts of the activated catalyst by weight were stirred in the solution for 16 hours, then filtered off and the product analysed after distilling off the solvent.

In the continuous reaction in accordance with the invention, the solution was pumped at 30 mls/hour up a column 1.5 cm in diameter and containing a lower bed of 5 gms of acid-washed Celite mixed with 5 mls of distilled water to ensure that the feed introduced into the base of the column was substantially saturated with water. An upper bed separated from the lower by a glass wool plug consisted of 6.7 gms of a wetted catalyst, the rate providing a mean residence time of 22 minutes.

Analysis showed that the conditions selected provided closely similar fatty acyl residues in the triglycerides of the respective products, with slightly more saturated residues in the product from the packed bed reactor, thus permitting close comparison with the products as shown in Table 1 below. Fatty acid analysis of the mid-fraction of palm oil was as follows in wt %:

$C_{14:0}$ 1.0; $C_{16:0}$ 56.9; $C_{18:0}$ 6.9; $C_{18:1}$ 30.9; $C_{18:2}$ 4 3.

Triglyceride analysis of both products showed the presence of approximately 18% myristic acid compared with 1% in the feed.

TABLE 1

| | | Product composition | |
|---|---|---|---|
| Species | Reactant Composition (%) | Stirred tank reactor (%) | Packed bed reactor (%) |
| Triglyceride | 70 | 52 | 63 |
| Fatty acid | 29 | 36 | 32 |
| Diglyceride | 1 | 12 | 5 |
| Triglyceride species | | | |
| SSS | — | 11 | 10 |
| SOS | — | 62 | 68 |

TABLE 1-continued

| Species | Reactant Composition (%) | Product composition | |
|---|---|---|---|
| | | Stirred tank reactor (%) | Packed bed reactor (%) |
| SSO | — | 1 | 1 |
| SLS | — | 9 | 7 |
| Others | — | 17 | 14 |

S = saturated

Table 1 shows that a substantial increased in triglyceride composition is provided from the packed bed reactor with significantly less free fatty acid and substantially less diglyceride. The triglyceride analysis also shows a significant increase in the valuable 2-oleyl disaturated glyceride content over the batch product, with no increase in the corresponding asymmetric triglyceride and certainly no increase either, in symmetrical linoleic homologue. As is apparent the total SOS content in the product made according to the invention is $(68 \times 0.63)\% = 42.8\%$ compared with 32.2% for the stirred reaction product.

EXAMPLE 2

A mixture of a liquid fraction of refined, neutralised shea oil fractionated at 5° C. from three times its weight of acetone, and stearic acid in the ratio 5:1, was dissolved in 2.8 parts by volume of petrol ether of BP 100° to 120° C. and pumped at a rate of 33 mls/hour and a temperature of 40° C., successively up a water saturation column and a reaction column of similar size in which the mixture was rearranged. Both columns were maintained at 40° C. by water jackets. The saturation column was packed with 5 grammes of acid-washed celite carrying 4.5 mls adsorbed water to saturate the feedstock. The reaction column was packed with 7 grammes of catalyst comprising Mucor miehei lipase precipitated on Celite and prepared in accordance with the method described in British patent specification no. 1,509,543. The lipase activity was 1.0 U/mgm and the catalyst was pre-activated by treatment with 0.7 mls water. The mean residence time in the reaction column was 28 mins.

EXAMPLE 3

Example 2 was repeated using as feedstock a mixture of a liquid fraction of palm oil, neutralised and pretreated in hexane solution with silica to remove polar impurities, with half its weight of stearic acid, the mixture being dissolved to form a 1:3.3 w/v solution in the petroleum ether.

The saturation column contained 4 grammes acid-washed celite carrying 3.6 mls water and the reaction column 7.5 grammes of a *Rhizopus japonicus* lipase catalyst precipitated as described, onto celite with an activity of 2.1 U/mg. The catalyst was pre-activated by adsorption of 0.75 mls of water.

The flow rate of the reaction column was 45 mls/hour giving a residence time of 22 minutes.

After running for 12 hours the product solutions from Examples 2 and 3 were collected, solvent removed and the oil products neutralised by methanol extraction. 470 grammes of the oil product were fractionated in acetone containing 0.5% water, in a 3-liter glass jacketed vessel fitted with a scraped surface stirrer. An StOSt-rich fraction was crystallised from the shea product using a solvent:oil ratio of 5:1. The solution was stirred at 40° C. for an hour, cooled thereafter at a rate of 60° C./hour to 12° C. and maintained at that temperature for an hour before the precipitated crystals were filtered off and washed twice with 940 grammes of acetone, giving a product yield of 27%.

The palm product was also fractionated, but in two stages, to recover a POSt-rich mid-fraction. In the first fractionation stage the neutralised oil product was dissolved in the aqueous acetone in the ratio 1:3 (w/w), held for an hour at 40° C. and cooled to 20° C. at a rate of 60° C. per hour. After holding for 1 hour at 20° C the crystals which formed were filtered off and washed with 740 mls of acetone, 37 grammes of crystals being removed. The liquid fraction was again fractionated, this time in a solution in 1:8 (w/w) aqueous acetone at 10° C. after similar cooling and holding procedures, recovering an overall yield of 40% of POSt-rich crystals, calculated on the original neutralised product.

The products from Examples 2 and 3 were compared with that from reactions in which the same catalysts were used batchwise, by dispersion in the feedstock solution. 450 grammes of the palm oil fraction and 225 grammes of stearic acid were dispersed in 1620 mls 100°–120° C. petroleum ether with 35 grammes of the *Rhizopus japonicus* catalyst of activity 2.1 U/mg, prepared as described and preactivated with 3.5 mls of water, for 4 hours.

1 Kg of the shea oil and 0.2 Kg of stearic acid in 3.61 liters at 100°–120° C. petrol ether were stirred for $8^1\!166$ hours with 100 grammes of the Mucor miehei catalyst, pre-activated by the addition of 10 mls of water. Both batch reactions were carried out at 40° C. and product recovery was as described for the packed bed reaction.

Fatty acid analysis of the neutralised products by methyl ester method, showed a significant increase in stearate content, reflecting a substantially complete degree of interaction with the stearic acid reactant. The shea feedstock increased from 29.8% to 36.2% in Example 1, compared with 34.3% in the batch product. The palm oil feedstock increased from 4.3% to 28.3% in Example 2 and to 28.7% in the batch reaction. Yield of POSt fraction from the batch palm product was 36%.

The batch test produced markedly higher free fatty acid in the crude product from both oils and a substantially higher diglyceride content in the neutralised product, reflected in a significantly lower yield of total triglycerides in the batch Analysis of individual triglycerides by silver phase High Pressure Liquid Chromatography method of the fractionated products from both the batch and packed bed reactors showed no significant difference from the composition of a commercially available shea fraction, also obtained by fractionation from acetone, which exhibited the following analysis:

$S_3$ 2.2%; SOS 77.5%; SSO 1.8%; SLnS 8.3%; SOO 5.9%; others 3.5%.

This was confirmed by determination of solids content of the product fractions by pulse NMR which indicated no significant differences in characteristics. Jensen cooling curves were also obtained from the shea fractionated product and on blends with equal parts of palm mid-fraction. Although all the Jensen data indicated good products, the packed bed product was superior to that from the batch reaction and closely comparable with the commercial shea product.

The batch and packed bed palm products were closely similar in composition to one another and to cocoabutter itself.

Further particulars of the shea product are given in Tables 2 and 3.

acids whereby triglycerides containing the free fatty acid are produced.

TABLE 2

|  | % FFA | Diglycerides % | Total* Triglycerides % | Triglycerides normalised to 100% | | | | Fractionation | |
|---|---|---|---|---|---|---|---|---|---|
|  |  |  |  | SOS | SLnS | SOO | SSS* | Yield % | Diglyceride % |
| Feed | 2.1 | 0.5 | 97.4 | 10.0 | 5.0 | 51.5 | 8.5 | — | — |
| Product | 23.3 | 3.5 | 73.2 | 27.4 | 7.1 | 33.1 | 10.4 | 27 | 0.5 |
| Batch product | 29.2 | 9.5 | 61.3 | 24.9 | 7.0 | 33.1 | 12.6 | 21 | 3.9 |

*includes triterpene alcohol esters.

TABLE 3

|  | Jensen cooling curve parameter of stearine | | | | | | Jensen cooling curve parameter of stearine/PMF 50:50 | | | | | |
|---|---|---|---|---|---|---|---|---|---|---|---|---|
|  | Tmax | Tmin | T | Tmax | Tmin | T | Tmax | Tmin | T | Tmax | Tmin | T |
| Stearine ex packed bed | 36.5 | 28.1 | 8.4 | 54 | 11 | 43 | 20.0 | 24.5 | 5.5 | 57 | 24 | 35 |
| Stearine ex batch | 35.6 | 28.7 | 6.9 | 55 | 12 | 43 | 28.3 | 24.8 | 3.5 | 66 | 26 | 40 |
| Commercial shea Stearine | 36.7 | 28.4 | 8.3 | 62 | 13 | 49 | 29.5 | 24.4 | 5.1 | 61 | 26 | 35 |

We claim:

1. A continuous interesterification process comprising the steps of:
   (a) precipitating a 1,3-specific lipase on inert particulate support material;
   (b) activating the lipase by addition of water in an amount effective to activate the lipase;
   (c) packing the inert support material carrying the precipitated lipase in a fixed bed;
   (d) preparing a fatty reactant mixture selected from the group consisting of fatty acids containing 3 to 20 carbon atoms, their esters including triglyceride oils and fats, their fractionated and hydrogenated derivatives, and combinations thereof;
   (e) dissolving water in said mixture in an amount sufficient to favor interesterification and minimize hydrolysis;
   (f) continuously flowing said mixture of step (e) through the fixed bed whereby a total contact time of less than two hours is achieved and glycerides in the 1,3-positions are formed; and
   (g) recovering from the solution of step (f), the glycerides enriched in the 1,3-positions.

2. Process according to claim 1 wherein the lipase is selected from the group consisting of *Aspergillus niger* and *Mucor* species and *Rhizopus* species.

3. Process according to claim 1 wherein the fatty reactants comprise a mixture of free and combined fatty acids whereby triglycerides containing the free fatty acid are produced.

4. Process according to claim 1 which is carried out at a temperature from 0 to 60°C.

5. A continuous interesterification process comprising the steps of:
   (a) precipitating on inert particulate support material, a 1,3-specific lipase isolated from a microbial source selected from the group consisting of *Aspergillus niger, Mucor* species and *Rhizopus* species;
   (b) activating the lipase by addition of water in an amount effective to activate the lipase;
   (c) packing the inert support material carrying the precipitated lipase in a fixed bed;
   (d) preparing a mixture of fatty acid selected from the group consisting of myristic, palmitic, stearic acid and combinations thereof, with a vegetable oil or glyceride ester derivative thereof;
   (e) dissolving water in the mixture in an amount sufficient to favor interesterification and minimize hydrolysis;
   (f) continuously flowing said mixture of step (e) through the fixed bed at a temperature from 0° to 60? C. whereby a total contact time of less than two hours is achieved and glycerides enriched in the 1,3-positions are formed; and
   (g) recovering from the mixture of step (f), the glycerides enriched in the 1,3-positions.

* * * * *